United States Patent
Kozawa (10) Patent No.: US 10,359,404 B2
(45) Date of Patent: Jul. 23, 2019

(54) NOISE LEVEL ESTIMATION METHOD, MEASUREMENT DATA PROCESSING DEVICE AND PROGRAM FOR PROCESSING MEASUREMENT DATA

(71) Applicant: SHIMADZU CORPORATION, Kyoto-shi, Kyoto (JP)

(72) Inventor: Hiroaki Kozawa, Omihachiman (JP)

(73) Assignee: SHIMADZU CORPORATION, Kyoto-shi, Kyoto (JP)

( * ) Notice: Subject to any disclaimer, the term of this patent is extended or adjusted under 35 U.S.C. 154(b) by 51 days.

(21) Appl. No.: 15/544,036

(22) PCT Filed: Jan. 26, 2015

(86) PCT No.: PCT/JP2015/051973
§ 371 (c)(1),
(2) Date: Jul. 17, 2017

(87) PCT Pub. No.: WO2016/120959
PCT Pub. Date: Aug. 4, 2016

(65) Prior Publication Data
US 2018/0011067 A1  Jan. 11, 2018

(51) Int. Cl.
*G01N 30/00* (2006.01)
*G01N 30/86* (2006.01)

(52) U.S. Cl.
CPC ....... *G01N 30/861* (2013.01); *G01N 30/8641* (2013.01); *G01N 30/8675* (2013.01); *G01N 30/8686* (2013.01)

(58) Field of Classification Search
CPC .................................................. G01N 30/861
(Continued)

(56) References Cited

U.S. PATENT DOCUMENTS

| | | | |
|---|---|---|---|
| 5,966,684 A * | 10/1999 | Richardson | H04B 1/123 702/190 |
| 2005/0285023 A1* | 12/2005 | Liu | G01N 21/274 250/221 |
| 2010/0283785 A1 | 11/2010 | Satulovsky | |

FOREIGN PATENT DOCUMENTS

| | | |
|---|---|---|
| JP | 07-098270 A | 4/1995 |
| WO | 2011/106527 A2 | 9/2011 |

OTHER PUBLICATIONS

Wentzell et al., "Characterization of heteroscedastic measurement noise in the absence of replicates", Analytica Chimica Acta, 2014, vol. 847, pp. 16-28.
(Continued)

*Primary Examiner* — Hien D Khuu
(74) *Attorney, Agent, or Firm* — Sughrue Mion, PLLC (57) ABSTRACT

In a method for estimating a noise level representing the magnitude of a noise component from measurement data, first waveform data composed of high frequency noise components extracted from assumed noise data are divided into segments so that each section where positive values successively occur or each section where negative values successively occur in the first waveform data is defined as one segment. A segment-width threshold is determined based on the distribution of the widths of the segments. Second waveform data composed of high frequency noise components extracted from measurement data are divided into segments in the same manner. Each segment having a width larger than the threshold is excluded from the segments in the second waveform data, to create a first segment group. The noise level is determined based on the heights or areas of the plurality of segments included in the first segment group.

12 Claims, 7 Drawing Sheets

(58) Field of Classification Search
USPC ............................................................ 702/32
See application file for complete search history.

(56) References Cited

OTHER PUBLICATIONS

Communication dated Dec. 14, 2017 from the European Patent Office in counterpart Application No. 15879857.9.

* cited by examiner

NOISE LEVEL ESTIMATION METHOD, MEASUREMENT DATA PROCESSING DEVICE AND PROGRAM FOR PROCESSING MEASUREMENT DATA

CROSS REFERENCE TO RELATED APPLICATIONS

This application is a National Stage of International Application No. PCT/JP2015/051973 filed Jan. 26, 2015, the contents of all of which are incorporated herein by reference in their entirety.

TECHNICAL FIELD

The present invention relates to a method for estimating the magnitude of a noise component (noise level) in a chromatogram, spectrum or other kinds of measurement data composed of a peak component, baseline component and noise component, as well as a device for processing such measurement data and a program for processing measurement data.

BACKGROUND ART

One type of device for analyzing components contained in a liquid sample is the liquid chromatograph. In a liquid chromatograph, a liquid sample is carried by a stream of mobile phase and introduced into a column. The components in the sample are temporally separated within the column and subsequently detected with a detector, such as an absorptiometer, to create a chromatogram. Each component is identified from the position of a peak on the chromatogram, and the concentration of that component is determined from the height or area of that peak (for example, see Patent Literature 1).

In general, a chromatogram obtained by a measurement can be separated into three components, i.e. the peak component, baseline component and noise component. The magnitude of the peak component changes with the elution of various components contained in the liquid sample, while that of the baseline component changes due to such factors as a change in the pressure of the pump supplying the mobile phase or a change in the ambient temperature (baseline drift). The change of the baseline component is normally slower than that of the peak component or noise component. By comparison, the magnitude of the noise component (noise level) fluctuates due to various factors, and its fluctuating amplitude is considerably high. Therefore, it is difficult to isolate the noise component from the chromatogram.

Figure 1:
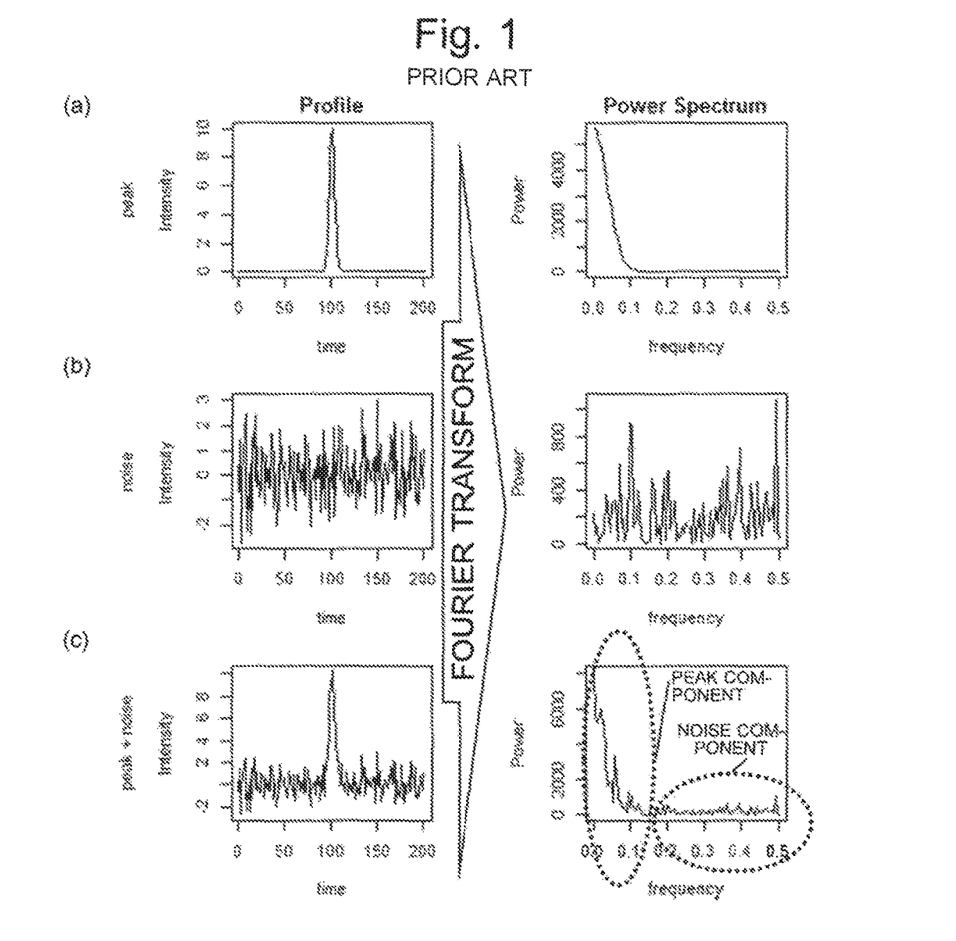
FIG. 1 shows waveforms of a peak component, noise component and their sum as well as their respective power spectra.

FIG. 1 shows one example of the waveforms (profiles) of a peak component (a), noise component (b) and their sum (c) as well as the power spectra respectively obtained by Fourier-transforming those profiles. As can be seen in those power spectra, the peak component is localized within a low frequency band, while the noise component is spread over a wide frequency band.

Accordingly, in order to extract the noise component from a chromatogram, high-pass filters which reduce frequency components lower than a predetermined frequency have been used. By the filter, the peak component localized within the low frequency band can be mostly removed. As the high-pass filter, for example, a second-order difference filter is used. Using a second-order difference filter as the high-pass filter yields a signal having a similar shape to a profile obtained by the second-order differentiation of the chromatogram. Though not shown in FIG. 1, the baseline component is also normally localized within the low frequency band and therefore can be mostly removed by the high-pass filter, as with the peak component.

CITATION LIST

Patent Literature

Patent Literature 1: JP 7-98270 A

SUMMARY OF INVENTION

Technical Problem

As just described, by using a high-pass filter, a considerable portion of the peak component and baseline component can be removed from a chromatogram to isolate the noise component. However, it is impossible to completely isolate the noise component from the other ones. Accordingly, it has been difficult to estimate the noise level in a chromatogram with high accuracy by merely using the high-pass filter. This problem becomes particularly noticeable when the peak intensity of the chromatogram is high or when there is a large number of peaks.

Although the previous description is concerned with the case of a chromatogram, similar problems can also occur in various other kinds of measurement data which contain a peak component, baseline component and noise component, as in a spectrum obtained in a spectroscopic measurement.

The problem to be solved by the present invention is to provide a noise level estimation method, measurement data processing device, and program for processing measurement data by which the noise component contained in measurement data which contain the three components of a peak component, baseline component and noise component can be assuredly isolated, so that the noise level can be estimated with high accuracy.

Solution to Problem

The first aspect of the present invention developed for solving the previously described problem is a method for estimating a noise level representing the magnitude of a noise component from measurement data containing the three components of a peak component, baseline component and noise component, the method including:

a) extracting, from assumed noise data purely composed of assumed noise for the measurement data, high frequency noise components by means of a high-pass filter which reduces frequency components lower than a predetermined frequency, dividing first waveform data which are waveform data of the high frequency noise components into a plurality of segments so that each section where positive values successively occur or each section where negative values successively occur in the first waveform data is defined as one segment, or so that each section between a local maximum and a local minimum neighboring each other in the first waveform data is defined as one segment, and determining a segment-width threshold based on the distribution of the widths of the plurality of segments;

b) extracting high frequency measurement components from the measurement data by means of the high-pass filter, and dividing second waveform data which are waveform data of the high frequency measurement components into a plurality of segments so that each section where positive values successively occur or each section where negative values successively occur in the second waveform data is defined as one segment, or so that each section between a local maximum and a local minimum neighboring each other in the second waveform data is defined as one segment;

c) excluding each segment having a width larger than the threshold from the plurality of segments obtained by dividing the second waveform data, to create a first segment group formed by the remaining segments; and d) determining the noise level based on the heights or areas of the plurality of segments included in the first segment group.

Examples of data that can be used as the assumed noise data include: a set of data purely composed of colored noise, such as white noise having a power spectrum whose magnitude is uniform and independent of the frequency, pink noise having a power spectrum whose magnitude is inversely proportional to the frequency, or brown noise whose having a power spectrum whose magnitude is inversely proportional to the square of the frequency; and a set of data prepared from actually measured noise.

The threshold of the widths of the plurality of segments may be defined, for example, as the upper limit value of the distribution of the widths of the plurality of segments obtained by dividing the first waveform data, or as the upper limit value of a distribution including a predetermined proportion (e.g. 90%) of those segments.

The estimation of the noise level based on the heights or areas of the plurality of segments included in the first segment group can be achieved, for example, by calculating the average value or median of the heights or areas of those segments.

In the noise level estimation method according to the present invention, the second waveform data obtained by extracting high frequency measurement components by using the high-pass filter is divided into a plurality of segments. Subsequently, each segment whose width is larger than the segment-width threshold calculated from assumed noise data is excluded, being identified as a segment which has originated from a component different from the noise component, i.e. which has originated from the peak component or baseline component. Therefore, even if a portion of the peak component or baseline component passes through the high-pass filter, the segment corresponding to that portion is excluded at this stage. Thus, the noise component is assuredly isolated from the measurement data, so that the noise level can be estimated with high accuracy.

Preferably, the noise level estimation method according to the present invention may further include:

e) extracting an outlier from the heights or areas of the plurality of segments included in the first segment group by comparing each of the heights or areas with the noise level obtained by the estimation;

f) excluding a segment having the outlier from the plurality of segments of the first segment group, to create a second segment group;

g) determining a noise level based on the heights or areas of the plurality of segments included in the second segment group.

By excluding an outlier of the height or area of the segment from the estimation of the noise level in this manner, a segment which has originated from a component different from noise yet has not been excluded by a mere comparison of the width can be excluded so as to estimate the noise level with an even higher level of accuracy. The estimation accuracy of the noise level can be further improved by repeating the process of removing a segment having an outlier and estimating the noise level until all outliers are removed or until a predetermined number of repetitions is reached.

The noise level estimation method according to the present invention may also include:

h) determining, for each of the plurality of segments in the first segment group, a segment position representative of the segment concerned;

i) extracting, for each of the plurality of segments in the first segment group, target segments which are segments having their respective segment positions located within a predetermined range from the segment position of the segment concerned; and j) determining the noise level at the segment position of the segment concerned, based on the heights or areas of the segment concerned and the target segments.

By estimating, for each of the plurality of segments in the high frequency measurement data, a noise level for a set of segments located within a predetermined range from the segment concerned in the previously described manner, a local noise level at the segment position of each segment can be determined.

For example, in a gradient analysis in which measurement conditions are temporally changed, the noise level may also temporally change. By estimating, for each of the plurality of segments, the noise level at the segment position of the segment concerned in the previously described manner the noise level can be estimated with high accuracy even in the case where the noise level temporally changes.

The previously described technique of excluding a segment having an outlier to improve the estimation accuracy of the noise level can also be applied in the determination of the noise level at the segment position of each segment. The estimation accuracy of the noise level can be further improved by repeating the process of excluding a segment having an outlier and estimating the noise level until all outliers are removed or until a predetermined number of repetitions is reached.

The second aspect of the present invention developed for solving the previously described problem is a measurement data processing device used for estimating a noise level from measurement data containing the three components of a peak component, baseline component and noise component, the device including:

a) a high-pass filter for reducing frequency components lower than a predetermined frequency;

b) a storage section for holding a segment-width threshold, the threshold previously determined by extracting, from assumed noise data purely composed of assumed noise for the measurement data, high frequency noise components by means of the high-pass filter, dividing first waveform data which are waveform data of the high frequency noise components into a plurality of segments so that each section where positive values successively occur or each section where negative values successively occur in the first waveform data is defined as one segment, or so that each section between a local maximum and a local minimum neighboring each other in the first waveform data is defined as one segment, and determining the threshold based on the distribution of the widths of the plurality of segments;

c) a second waveform data acquirer for extracting high frequency measurement components from the measurement data by means of the high-pass filter, and for acquiring second waveform data which are waveform data of the high frequency measurement components;

d) a segment divider for dividing the second waveform data into a plurality of segments so that each section where positive values successively occur or each section where negative values successively occur in the second waveform data is defined as one segment, or so that each section between a local maximum and a local minimum neighboring each other in the second waveform data is defined as one segment;

e) a first segment group creator for excluding each segment having a width larger than the threshold from the plurality of segments obtained by dividing the second waveform data, to create a first segment group; and f) a noise level calculator for determining the noise level based on the heights or areas of the plurality of segments included in the first segment group.

The third aspect of the present invention developed for solving the previously described problem is a program for processing measurement data, used for estimating a noise level from measurement data containing the three components of a peak component, baseline component and noise component, the program characterized by making a computer, provided with a storage section for holding a segment-width threshold and a high-pass filter, function as the second waveform acquirer, the segment divider, the first segment group creator and the noise level calculator described in the second aspect of the present invention.

Advantageous Effects of the Invention

With the noise level estimation method, measurement data processing device or program for processing measurement data according to the present invention, the noise component contained in measurement data which include the three components of a peak component, baseline component and noise component can be assuredly isolated, so that the noise level can be estimated with high accuracy.

DESCRIPTION OF EMBODIMENTS

Embodiments of the noise level estimation method, measurement data processing device, and program for processing measurement data according to the present invention are hereinafter described with reference to the attached drawings. The following embodiments deal with the case of estimating a noise level which is the magnitude of a noise component contained in a chromatogram acquired using a liquid chromatograph.

First Embodiment

Figure 2:
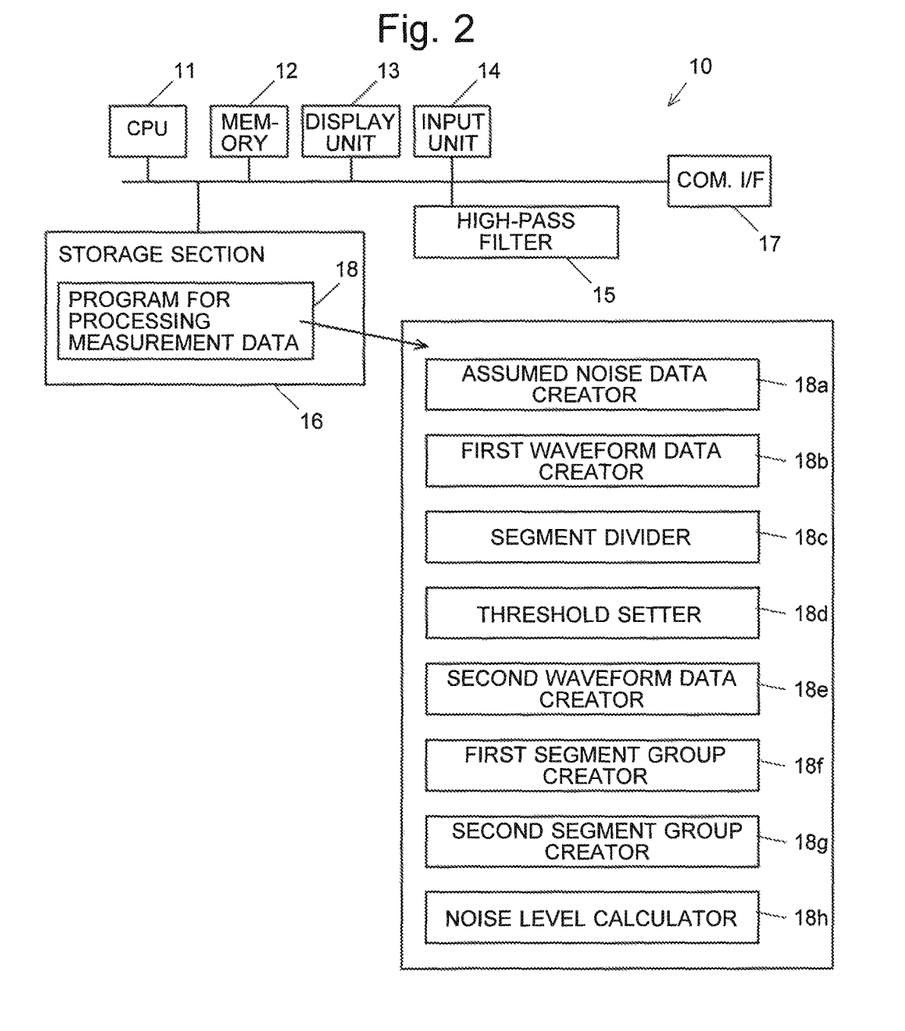
FIG. 2 is a configuration diagram of a measurement data processing device according to the first embodiment.

FIG. 2 shows the configuration of a measurement data processing device 10 according to the first embodiment. The measurement data processing device 10 is actually a general-purpose personal computer provided with a central processing unit (CPU) 11, memory 12, display unit (monitor) 13, input unit 14, high-pass filter 15, storage section 16 including a high-volume storage device (e.g. hard disk), communication interface (com. I/F) 17, and other elements. The measurement data processing device 10 can be connected to a liquid chromatograph (not shown) through the communication interface 17.

In the storage section 16, a program 18 for processing measurement data is stored in addition to the OS (operating system). Executing this program 18 for processing measurement data makes the CPU 11 function as an assumed noise data creator 18a, first waveform data creator 18b, segment divider 18c, threshold setter 18d, second waveform data creator 18e, first segment group creator 18f, second segment group creator 18g, and noise level calculator 18h, all of which will be described later.

Figure 3:
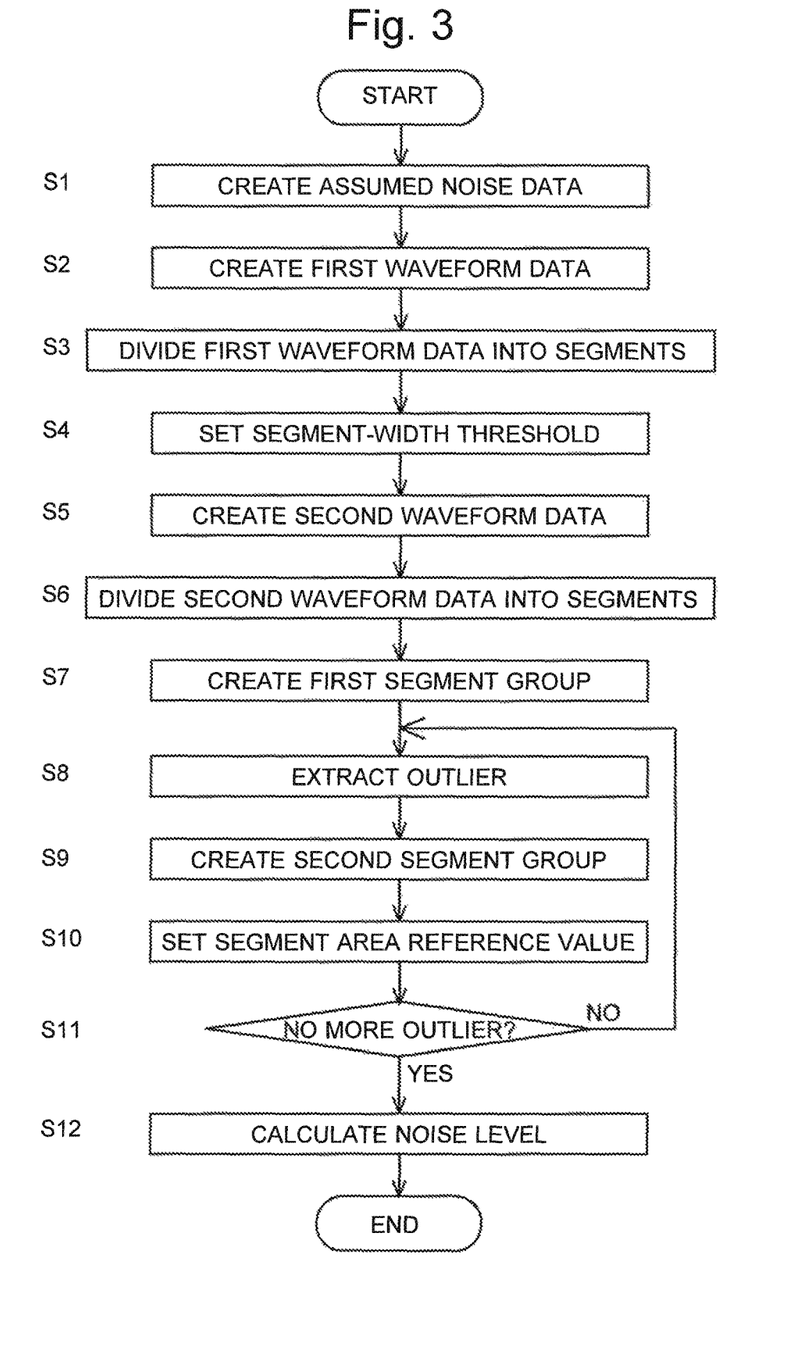
FIG. 3 is a flowchart in a noise level estimation method according to the first embodiment.

The noise level estimation method using the measurement data processing device 10 of the present embodiment is hereinafter described with reference to the flowchart of FIG. 3.

Initially, based on a user input, the assumed noise data creator 18a creates assumed noise data which are purely composed of assumed noise for measurement data (Step S1). The assumed noise in the present embodiment is normal white noise. Normal white noise is a type of noise having both the characteristics of white noise which has a constant intensity at all frequencies and those of Gaussian noise (normally distributed noise). The first waveform data creator 18b creates first waveform data which are waveform data of high frequency noise components obtained by attenuating low frequency components in the assumed noise data by using the high-pass filter 15 (Step S2). The high-pass filter 15 in the present embodiment is a second-order difference filter. A set of data different from those created from the normal white noise may also be used as the assumed noise data, such as a set of data created from colored noise, such as pink noise or brown noise, or a set of actually measured noise data.

Figure 4:
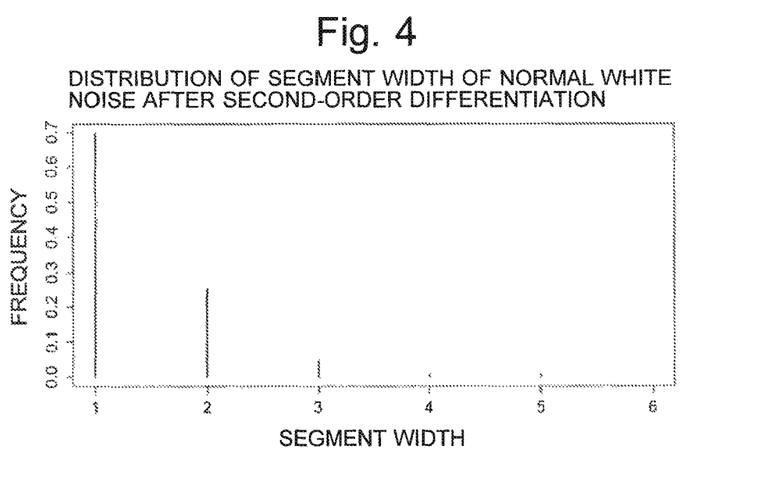
FIG. 4 shows a distribution of the segment width of normal white noise after a second-order difference calculation.

After the first waveform data are created, the segment divider 18c divides the first waveform data into a plurality of segments so that each section where positive values successively occur or each section where negative values successively occur in the first waveform data is defined as one segment (Step S3). Then, the threshold setter 18d creates a distribution of the widths of those segments (FIG. 4) and sets the segment-width threshold based on that distribution (Step S4). In the present embodiment, the largest value in the distribution of the segment width, i.e. six (arbitrary unit in the time-axis direction), is set as the threshold, and this value is saved in the storage section 16. It should be noted that the threshold set by Steps S1 through S4 can be applied to a plurality of sets of chromatogram data. Accordingly, by previously setting the threshold and saving it in the storage section 16, a noise component can be estimated from each of the plurality of sets of chromatogram data by merely performing Step S6 and subsequent steps, which will be hereinafter described.

Figure 5A:
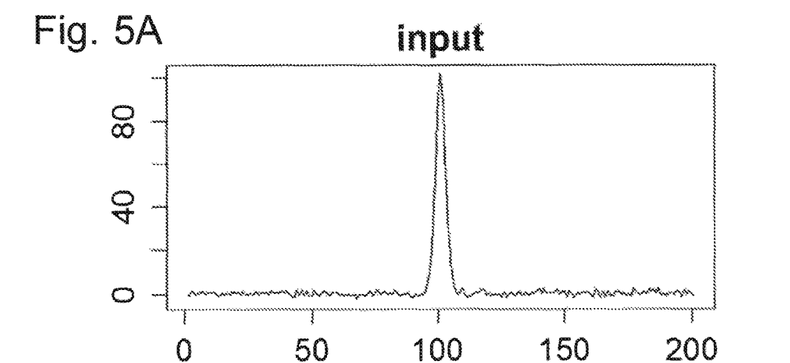
FIGS. 5A and 5B are the measurement data and first waveform data in the first embodiment, respectively.
Figure 5B:
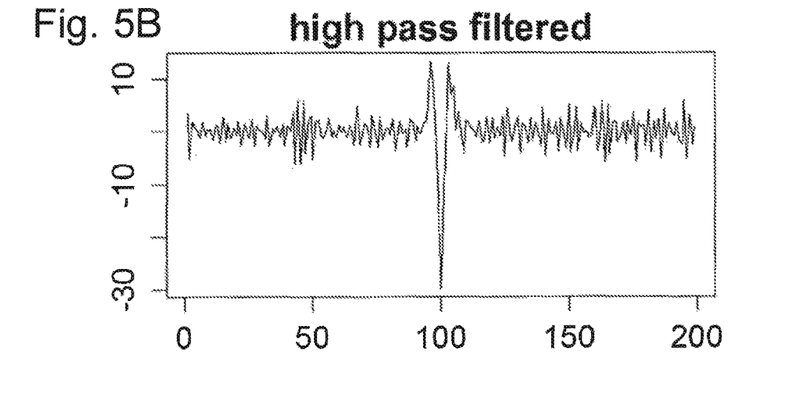
Figure 6A:
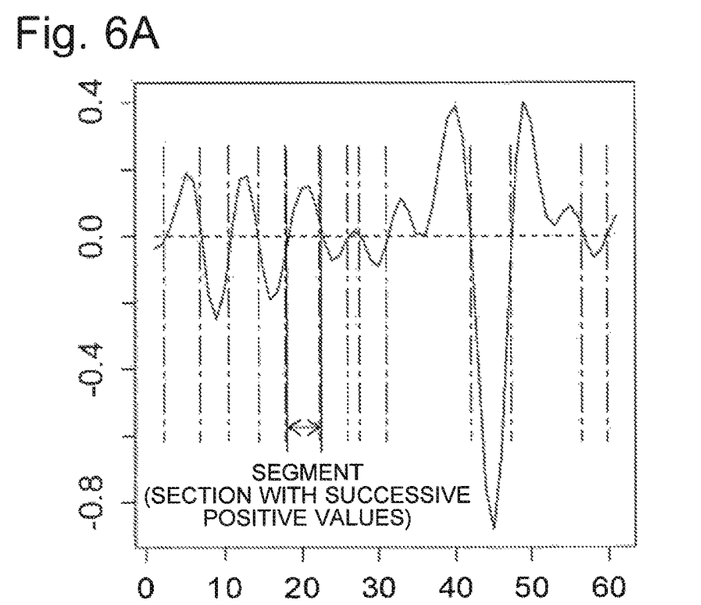
FIGS. 6A and 6B illustrate the division into segments and the exclusion of segments in the first embodiment, respectively.
Figure 6B:
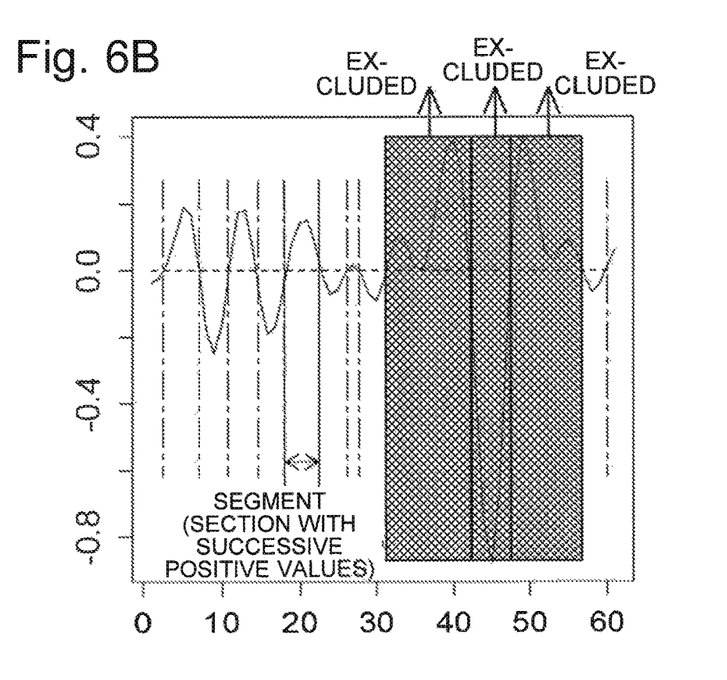

Subsequently, the second waveform data creator 18e reads measurement data of a chromatogram previously stored in the storage section 16 (FIG. 5A), and creates second waveform data, which are waveform data of high frequency measurement components, using the high-pass filter 15 (Step S5; FIG. 5B). After the second waveform data are created, the segment divider 18c divides the second waveform data into a plurality of segments so that each section where positive values successively occur or each section where negative values successively occur in the second waveform data is defined as one segment (Step S6; FIG. 6A). Then, the first segment group creator 18f compares the width of each of the segments in the second waveform data with the segment-width threshold which has been set from the first waveform data, and excludes each segment having a width larger than the threshold, to create a first segment group (Step S7; FIG. 6B). Step S7 is a process for excluding a peak component or baseline component based on the fact that a segment which corresponds to a peak component or baseline component that has passed through the high-pass filter has a larger width than that of a segment which originates from the noise component.

After the first segment group is created, the noise level calculator 18h computes the area of each of the segments included in the first segment group and sets the average of the computed areas as the segment-area reference value. Then, the second segment group creator 18g compares the area of each segment in the first segment group with the segment area reference value, extracts outliers included within a certain proportion (e.g. 5%) of the total number of the segments in descending order of the difference from the area reference value, and excludes the segments corresponding to the outliers (Step S8), to create a second segment group (Step S9). For example, the extraction of the outliers can be achieved, for example, by regarding any value larger than the average $+N\sigma$ of the segment areas of the segments as an outlier (where N is a positive integer, and $\sigma$ is the unbiased standard deviation). As for N, a suitable value for each set of measurement data can be used taking into account the distribution of the segment-area values.

The segment-area value may be the median of the distribution of the segment areas of the segments. In this case, the extraction of the outliers can be achieved, for example, by regarding any value larger than the median $+M\times MAD$ (median absolute deviation) of the areas of the segments as an outlier (where M is a positive integer).

The extraction of the outliers can also be achieved by various other methods, e.g. by extracting any value whose difference from the area reference value is larger than a previously set value.

The process of Steps S8 through S9 is intended for removing the influence of a noise component having a singular magnitude caused by an accidental factor during the measurement. In the process of removing the influence of a noise component having a singular magnitude, an extremely small area value of the segment may also be treated as an outlier, in which case any value which does not fall within the range given by the average value $\pm N\sigma$ of the segment areas, or the median $\pm M\times MAD$ of the segment areas, can be regarded as an outlier.

Those steps also remove segments which have originated from a peak or baseline yet have not been excluded by the process using the threshold of the width.

After the second segment group is created, the noise level calculator 18h once more computes the area of each segment included in the second segment group, and sets the average of the computed areas as the segment area reference value (Step S10). Then, based on this segment area reference value, the noise level calculator determines whether or not an outlier exists among the area values of the segments. If no outlier exists ("YES" in Step S11), the noise level calculator computes the noise level from the latest segment area reference value. If an outlier still exists ("NO" in Step S11), the extraction and exclusion of an outlier (Step S8) is once more performed by the second segment group creator 18g to create the second segment group (Step S9), and the segment area reference value is newly set (Step S10). Such a process is repeated until all outliers are removed. After that, the noise level is calculated.

If the value of N or M included in the calculation formula of the boundary value used for the extraction of the outliers is small, it may be impossible to remove all outliers by the repetition of Steps S8 through S10. To deal with such a case, the device may be configured to calculate the noise level, regardless of whether or not an outlier exists, after the number of repetitions of Steps S8 through S10 has reached a predetermined number (e.g. five).

The process from Steps S8 through S11 is intended for a high-accuracy calculation of the noise level and is not indispensable for the present invention. That is to say, the noise level may be directly calculated from the areas of the segments in the first segment group.

Thus, with the noise level estimation method, measurement data processing device or program for processing measurement data according to the first embodiment, even if a portion of the peak component or baseline component passes through the high-pass filter, the segment corresponding to that portion is excluded. Therefore, the noise component can be assuredly isolated from the measurement data, so that the noise level can be estimated with high accuracy. Additionally, according to the first embodiment, by excluding an outlier of the segment area from the estimation of the noise level, a segment which has originated from a component different from noise yet has not been excluded by a mere comparison of the width can be excluded, so that the noise level can be estimated with an even higher level of accuracy. It should be noted that, as opposed to the previous example in which the segment (area) reference value and the noise level are determined based on the area values of the segments, the segment (height) reference value and the noise level may be determined from the heights of the segments.

Second Embodiment

Figure 7:
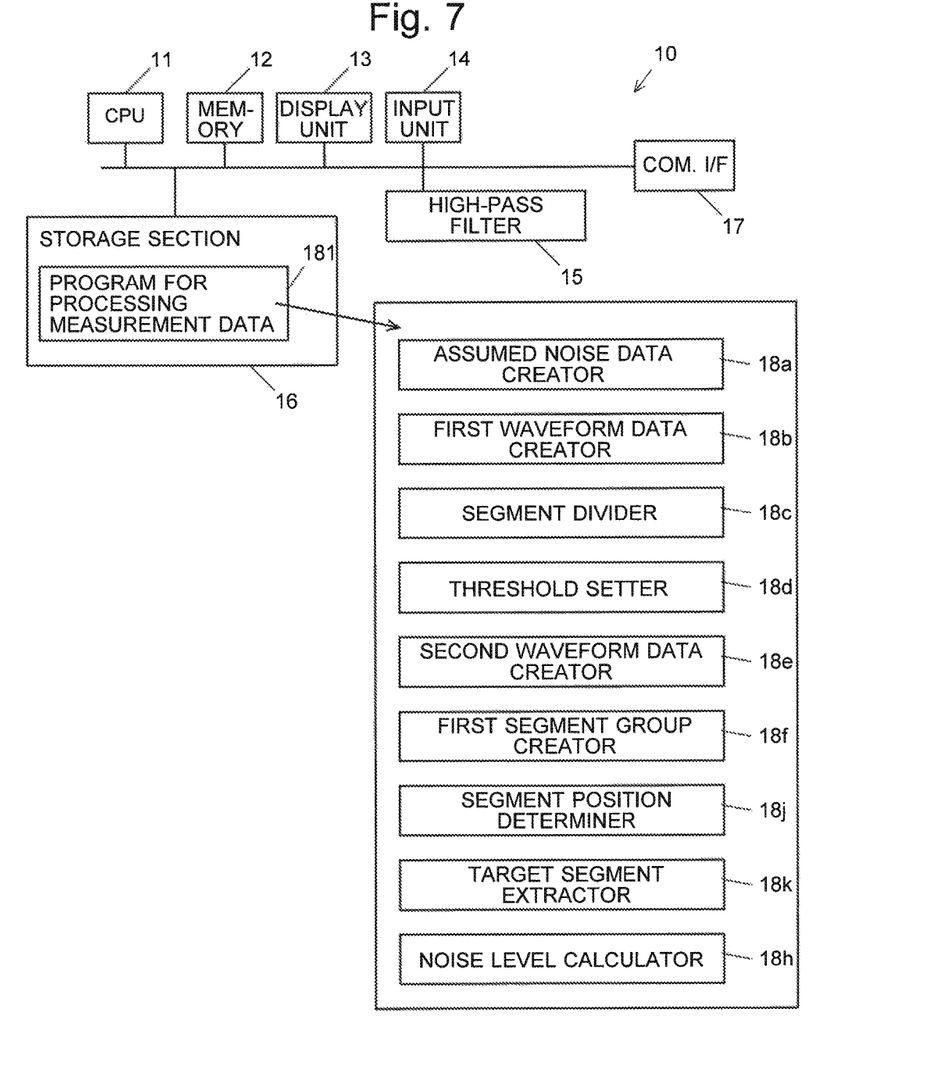
FIG. 7 is a configuration diagram of a measurement data processing device according to the second embodiment.

FIG. 7 shows the configuration of a measurement data processing device 10a according to the second embodiment. The same components as described in the first embodiment are denoted by the same numerals and will not be described. In the second embodiment, executing the program 181 for processing measurement data makes the CPU 11 function as an assumed noise data creator 18a, first waveform data creator 18b, segment divider 18c, threshold setter 18d, second waveform data creator 18e, first segment group creator 18f, segment position determiner 18j, target segment extractor 18k and noise level calculator 18h, all of which will be described later.

Figure 8:
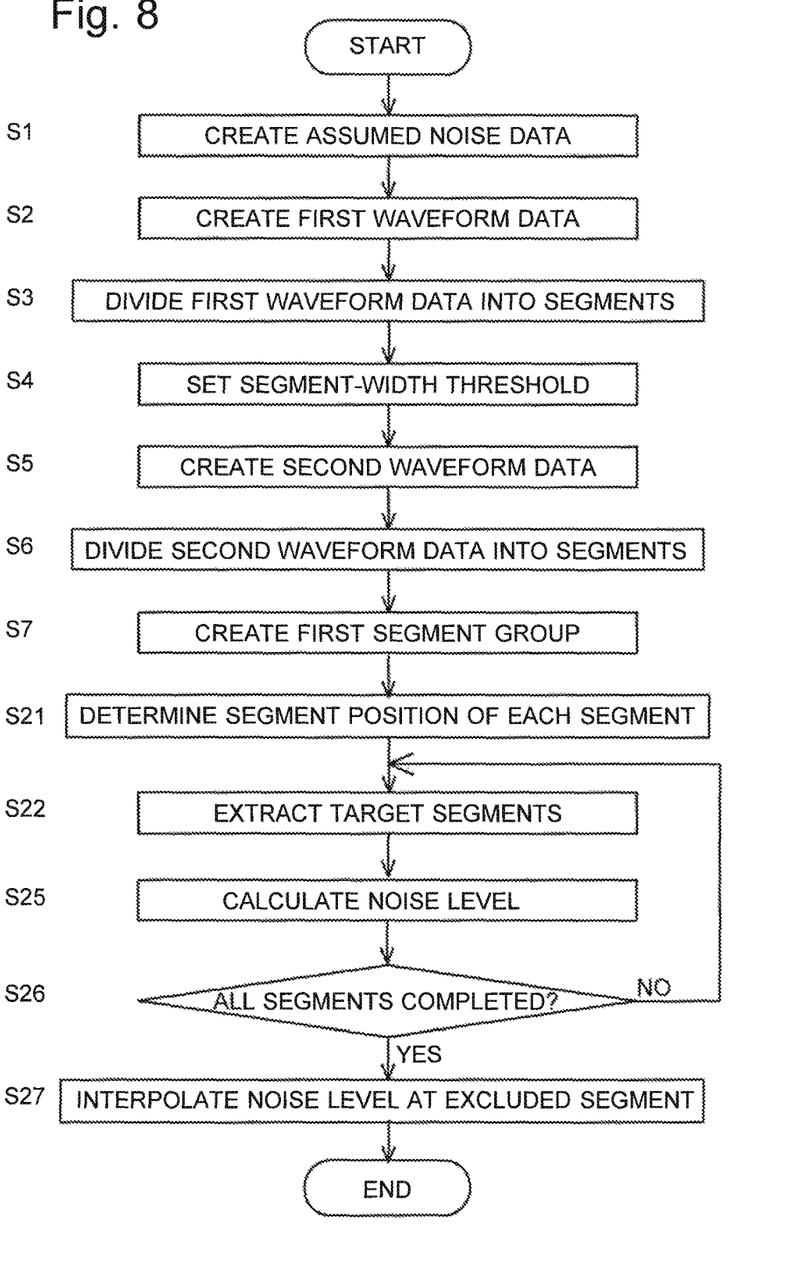
FIG. 8 is a flowchart in a noise level estimation method according to the second embodiment.

The noise level estimation method using the measurement data processing device 10a of the present embodiment is hereinafter described with reference to the flowchart of FIG. 8. The same processes as described in the first embodiment are denoted by the same numerals and will not be described.

The setting of the segment-width threshold using assumed noise data (Steps S1 through S4) and the creation of the first segment group which is a set of waveform data of high frequency components (Steps S5 through S7) are the same as in the first embodiment. The second embodiment is characterized by the subsequent Steps S21 through S27.

After the first segment group is created, the segment position determiner 18j designates, for each of the segments in the first segment group, the central position of the segment concerned as the segment position (Step S21). Subsequently, for one segment (which is hereinafter called the "segment in question") among those segments, the target segment extractor 18k extracts, as the target segments, one or more segments having their respective segment positions located within a preciously set range from the segment position of the segment in question (Step S22). Then, the noise level calculator 18h computes the noise level at the segment position of the segment in question based on the average (or median or the like) of the areas (or heights) of the target segments and the segment in question (Step S25).

Steps S22 through S25 are performed for every segment in the first segment group. After the calculation of the noise level at the segment position of each segment is completed for all segments ("YES" in Step S26), the noise level at the segment position of each segment excluded from the creation of the first segment group (i.e. each segment originating from the peak component or baseline component) is interpolated (Step S27). The interpolation of the noise level can be performed by an appropriate method for the mode of change in the noise level, such as the linear interpolation or spline interpolation.

Thus, with the noise level estimation method, measurement data processing device or program for processing measurement data according to the second embodiment, the peak component and baseline component can be assuredly excluded, and furthermore, the noise level at each position on the chromatogram can be calculated. Such a method or device according to the second embodiment can be suitably used in the case where the noise level fluctuates due to the measurement system, e.g. in a chromatogram obtained by a gradient analysis in which the baseline component easily fluctuates, causing a corresponding fluctuation in the noise level.

Both of the first and second embodiments are mere examples and can be appropriately changed in line with the gist of the present invention.

The previously described embodiments have been divided into two embodiments in order to separately describe their respective configurations and steps. It is also possible to configure a device which includes the configurations and steps of both of the first and second embodiments. With this configuration, it is possible to determine the noise level at each position on a chromatogram as well as improve the accuracy of that noise level.

The previously described embodiments are concerned with the case of processing a chromatogram obtained with a liquid chromatograph. The present invention can be used to determine not only the noise level in a chromatogram obtained with a liquid chromatograph or gas chromatograph but also in various other kinds of measurement data, such as a spectrum obtained by a spectrometric measurement.

In the previous embodiments, each section where positive values successively occur or each section where negative values successively occur in the waveform data of high frequency components extracted by using a second-order difference filter is defined as one segment. Other kinds of high-pass filters may also be used to extract high frequency components. It should be noted that a section where positive values successively occur (or a section where negative values successively occur) in the waveform data of high frequency components extracted by using an $n^{th}$-order difference filter (where n is an integer equal to or greater than two) corresponds to a section between a local maximum and a local minimum neighboring each other in the waveform data of high frequency components extracted by using an $n+1^{st}$-order difference filter. That is to say, the previously described processing of measurement data can be similarly performed by dividing the waveform data into segments so that each section between a local maximum and a local minimum neighboring each other is defined as one segment, instead of defining each section where positive values successively occur (or each section where negative values successively occur) as one segment.

REFERENCE SIGNS LIST 10, 10a . . . Measurement Data Processing Device
11 . . . CPU
12 . . . Memory
13 . . . Display Unit
14 . . . Input Unit
15 . . . High-Pass Filter
16 . . . Storage Section
18, 181 . . . Program for Processing Measurement Data
   18a . . . Assumed Noise Data Creator
   18b . . . First Waveform Data Creator
   18c . . . Segment Divider
   18d . . . Threshold Setter
   18e . . . Second Waveform Data Creator
   18f . . . First Segment Group Creator
   18g . . . Second Segment Group Creator
   18h . . . Noise Level Calculator
   18j . . . Segment Position Determiner
   18k . . . Target Segment Extractor
17 . . . Communication Interface

The invention claimed is:

1. A noise level estimation method for estimating a noise level representing a magnitude of a noise component from measurement data containing three components of a peak component, baseline component and noise component, the method comprising:

a) extracting, from assumed noise data purely composed of assumed noise for the measurement data, high frequency noise components by means of a high-pass filter which reduces frequency components lower than a predetermined frequency, dividing first waveform data which are waveform data of the high frequency noise components into a plurality of segments so that each section where positive values successively occur or each section where negative values successively occur in the first waveform data is defined as one segment, or so that each section between a local maximum and a local minimum neighboring each other in the first waveform data is defined as one segment, and determining a segment-width threshold based on a distribution of widths of the plurality of segments;

b) extracting high frequency measurement components from the measurement data by means of the high-pass filter, and dividing second waveform data which are waveform data of the high frequency measurement components into a plurality of segments so that each section where positive values successively occur or each section where negative values successively occur in the second waveform data is defined as one segment, or so that each section between a local maximum and a local minimum neighboring each other in the second waveform data is defined as one segment;

c) excluding each segment having a width larger than the threshold from the plurality of segments obtained by dividing the second waveform data, to create a first segment group formed by the remaining segments; and d) determining the noise level based on heights or areas of the plurality of segments included in the first segment group.

2. The noise level estimation method according to claim 1, further comprising:

e) extracting an outlier from the heights or areas of the plurality of segments included in the first segment group by comparing each of the heights or areas with the noise level;

f) excluding a segment having the outlier from the plurality of segments of the first segment group, to create a second segment group;

g) determining a noise level based on the heights or areas of the plurality of segments included in the second segment group.

3. The noise level estimation method according to claim 2, wherein:

the noise level is determined after a process including steps of extracting an outlier from the heights or areas of the segments included in the second segment group and removing a segment corresponding to the outlier to newly create the second segment group is repeated until all outliers are removed or until a predetermined number of repetitions is reached.

4. The noise level estimation method according to claim 1, further comprising:

h) determining, for each of the plurality of segments in the first segment group, a segment position representative of the segment concerned;

i) extracting, for each of the plurality of segments in the first segment group, target segments which are segments having their respective segment positions located within a predetermined range from the segment position of the segment concerned; and j) determining a noise level at the segment position of the segment concerned, based on the heights or areas of the segment concerned and the target segments.

5. The noise level estimation method according to claim 4, further comprising:

k) extracting an outlier from the heights or areas of the target segments by comparing each of the heights or areas with the height or area of the segment concerned;

l) excluding a segment having the outlier from the segment concerned or the target segments, to create a second segment group;

m) determining a noise level at the segment position of the segment concerned, based on the heights or areas of the segments included in the second segment group.

6. The noise level estimation method according to claim 5, wherein:

the noise level is determined after a process including steps of extracting an outlier from the heights or areas of the segments included in the second segment group and removing a segment corresponding to the outlier to newly create the second segment group is repeated until all outliers are removed or until a predetermined number of repetitions is reached.

7. The noise level estimation method according to claim 1, wherein the measurement data indicates components of a sample detected by an analysis device.

8. The noise level estimation method according to claim 7, wherein the analysis device is a chromatograph that separates the components temporally, and the measurement data is a chromatogram.

9. A non-transitory computer readable medium recording a program for processing measurement data, used for estimating a noise level from measurement data containing three components of a peak component, baseline component and noise component, the program characterized by making a computer, provided with a storage for holding a segment-width threshold and a high-pass filter, function in accordance with the noise level estimation method according to claim 1.

10. A measurement data processing device used for estimating a noise level from measurement data containing three components of a peak component, baseline component and noise component, the device comprising:

a) a high-pass filter for reducing frequency components lower than a predetermined frequency;

b) a storage for holding a segment-width threshold, the threshold previously determined by extracting, from assumed noise data purely composed of assumed noise for the measurement data, high frequency noise components by means of the high-pass filter, dividing first waveform data which are waveform data of the high frequency noise components into a plurality of segments so that each section where positive values successively occur or each section where negative values successively occur in the first waveform data is defined as one segment, or so that each section between a local maximum and a local minimum neighboring each other in the first waveform data is defined as one segment, and determining the threshold based on a distribution of widths of the plurality of segments; and a processor configured to extract high frequency measurement components from the measurement data by means of the high-pass filter, and for acquiring second waveform data which are waveform data of the high frequency measurement components;

divide the second waveform data into a plurality of segments so that each section where positive values successively occur or each section where negative values successively occur in the second waveform data is defined as one segment, or so that each section between a local maximum and a local minimum neighboring each other in the second waveform data is defined as one segment;

exclude each segment having a width larger than the threshold from the plurality of segments obtained by dividing the second waveform data, to create a first segment group; and determine the noise level based on heights or areas of the plurality of segments included in the first segment group.

11. The measurement data processing device according to claim 10, wherein the measurement data indicates components of a sample detected by an analysis device.

12. The measurement data processing device according to claim 11, wherein the analysis device is a chromatograph that separates the components temporally, and the measurement data is a chromatogram.

* * * * *